US006759229B2

(12) United States Patent
Schaak

(10) Patent No.: US 6,759,229 B2
(45) Date of Patent: Jul. 6, 2004

(54) TOXIN-PHAGE BACTERIOCIDE ANTIBIOTIC AND USES THEREOF

(75) Inventor: Diane L. Schaak, Somerville, MA (US)

(73) Assignee: President & Fellows of Harvard College, Cambridge, MA (US)

( * ) Notice: Subject to any disclaimer, the term of this patent is extended or adjusted under 35 U.S.C. 154(b) by 261 days.

(21) Appl. No.: 10/025,598

(22) Filed: Dec. 18, 2001

(65) Prior Publication Data

US 2003/0147852 A1 Aug. 7, 2003

(51) Int. Cl.$^7$ .......................... C12N 7/01; C12N 15/09; C12N 15/00; C12N 1/20; C07H 21/04
(52) U.S. Cl. .................. 435/235.1; 435/69.7; 435/69.1; 435/320.1; 435/91.4; 435/252.3; 536/23.1; 536/23.4
(58) Field of Search ............................... 536/23.1, 23.4; 435/69.1, 69.7, 320.1, 252.3, 471, 235.1, 91.4

(56) References Cited

U.S. PATENT DOCUMENTS

| | | | |
|---|---|---|---|
| 4,886,754 A | | 12/1989 | Graham et al. |
| 5,766,892 A | * | 6/1998 | Merril et al. ............... 424/93.6 |
| 5,811,093 A | * | 9/1998 | Merril et al. ............... 424/93.6 |
| 5,985,271 A | | 11/1999 | Fischetti et al. |
| 5,997,862 A | | 12/1999 | Fischetti et al. |
| 6,017,528 A | | 1/2000 | Fischetti et al. |
| 6,056,954 A | | 5/2000 | Fischetti et al. |
| 6,056,955 A | | 5/2000 | Fischetti et al. |
| 6,121,036 A | | 9/2000 | Ghanbari et al. |
| 6,238,661 B1 | | 5/2001 | Fischetti et al. |
| 6,248,324 B1 | | 6/2001 | Fischetti et al. |
| 6,254,866 B1 | | 7/2001 | Fischetti et al. |
| 6,264,945 B1 | | 7/2001 | Fischetti et al. |

FOREIGN PATENT DOCUMENTS

| | | |
|---|---|---|
| WO | WO 00/32825 | 6/2000 |
| WO | WO 00/69269 | 11/2000 |
| WO | WO 01/09382 | 2/2001 |
| WO | WO 01/14579 | 3/2001 |
| WO | WO 01/21817 | 3/2001 |

OTHER PUBLICATIONS

Alisky et al., "Bacteriophages Show Promise as Antimicrobial Agents", *Journal of Infection*, 36:5–15, 1998.
Davies, "Bacteria on the rampage", *Nature*, 383:219–220, 1996.
Fezoui, "De novo design, synthesis and structural characterization of an α–helical hairpin peptide (αtα): A novel model system for the study of protein folding intermediates", UMI Dissertation Services, pp. 195, 2001.
Fezoui et al., "A de novo designed helix–turn–helix peptide forms nontoxic amyloid fibrils", *Nature Structural Biology*, 7(12):1095–1099, 2000.
Fezoui et al., "De novo design and structural characterization of an α–helical hairpin peptide: A model system for the study of protein folding intermediates", *Proc. Natl. Acad. Sci. USA*, 91:3675–3679, 1994.
Fezoui et al., "Solution structure of αtα, a helical hairpin peptide of de novo design", *Protein Science*, 6:1869–1877, 1977.
Gould, "A review of the role of antibiotic policies in the control of antibiotic resistance", Journal of Antimicrobial Chemotherapy, *Journal of Antimicrobial Chemotherapy*, 43:459–465, 1999.
Hancock, R.E.W. and Diamond, G., "The role of cationic antimicrobial peptides in innate host defences", *Trends in Microbiology, Reviews*, 8(9):387–432, 2000.
Mackal et al., "The Formation of λ Bacteriophage by λ DNA in Disrupted Cell Preparations", *Proc. Natl. Acad. Sci.*, 51:1172–1178, 1964.
Michael, S.I. and Curiel, D.T., "Strategies to achieve targeted gene delivery via the receptor–mediated endocytosis pathway, Review", *Gene Therapy*, 1:223–232, 1994.
Monroe, S. and Polk, R, "Antimicrobial use bacterial resistance", *Current Opinion in Microbiology*, 3:496–501, 2000.
Peschke et al., "Efficient Utilization of *Escherichia coli* Transcriptional Signals in *Bacillus subtilis*", *J. Mol. Biol.*, 186(3):547–555, 1985.
Wong, H.C. and Chang, S., "Identification of a positive retroregulator that stabilizes mRNAs in bacteria", *Proc. Natl. Acad. Sci. USA*, 83:3233–3237, 1986.

* cited by examiner

*Primary Examiner*—Gerry Leffers
(74) *Attorney, Agent, or Firm*—Fish & Richardson P.C.

(57) ABSTRACT

The invention provides intracellular peptide toxins capable of killing bacterial and eukaryotic cells when present within the cell, while substantially lacking the ability to kill such cells when present externally. The invention also provides recombinant bacteriophage containing nucleic acid sequences encoding intracellular peptide toxins, and methods of using such bacteriophage to kill bacteria. Furthermore, the invention provides compositions, including pharmaceutical compositions, which can be used to kill bacteria or inhibit the growth of bacteria both in vitro and in vivo. Methods of treating a bacterial infection in a subject are also provided by the invention.

9 Claims, No Drawings

TOXIN-PHAGE BACTERIOCIDE ANTIBIOTIC AND USES THEREOF

TECHNICAL FIELD

This invention relates to compositions and methods for killing bacteria.

BACKGROUND

Throughout recorded history virulent bacterial infections have been a bane to mankind. Until recently, it was assumed that drug antibiotics had largely eradicated virulent bacteria. It is now apparent, however, that bacteria have circumvented the effects of single-point targeted drug antibiotics. Consequently, there is a need to develop new anti-bacterial agents that can be used to supplement or replace conventional drug antibiotics.

Like animal cells, bacterial cells are subject to infectious agents that are present in their environment. Viruses known as bacteriophage, or phage, specifically infect bacterial cells. Bacteriophage are the natural enemies of bacteria and, over the course of evolution, have developed proteins which enable them to infect a bacterial host cell, replicate their genetic material, usurp host metabolism, and ultimately kill their bacterial host cell.

Research into the use of bacteriophage as therapeutic agents for treatment of bacterial infection began sometime in the late 19th century, predating the development of conventional drug antibiotics. By 1920, Edward Twort and Felix d'Herelle, two noted pioneers in bacteriophage research, were isolating bacteriophage from several bacterial species and using them as anti-bacterial agents. During the early 1940's, however, antibiotics were introduced to the world as a broad range treatment for bacterial infections, and bacteriophage therapy research went into decline.

Early clinical studies of phage therapy were plagued with poor experimental design, with few controls and little documentation, variable success due to the indiscriminate use of phage to treat a broad range of bacterial infections, and the use of procedures that introduced bacterial toxins into patients and loss of effectiveness of the isolated phage.

The lack of knowledge and scientific expertise needed to understand bacteriophage and their interaction with bacteria also hindered efforts to improve phage therapy. For example, differences between the biological interaction of bacteriophage strains with their species-specific bacterial host in vitro as compared to in vivo have posed considerable difficulty. Although bacteriophage can be selected for their lytic virulence (immediately replicating and then inducing bacterial host cell lysis following infection) in vitro, such selection does not guarantee against the conversion of a seemingly lytic phage to a temperate phage (entering into a state of lysogeny via integration of the bacteriophage genome into the bacterial genome followed by a quiescent period during which lytic proteins are not expressed) in vivo. These conversions result in lysogenic bacteria that are resistant to further bacteriophage infection, thus reducing the effectiveness of phage therapy.

Since the early 1940's drug antibiotics have become the choice for treating virulent bacterial infections. Several problems associated with this approach are now becoming evident. The misuse and overuse of drug antibiotics has contributed to the rise of antibiotic resistant bacterial strains. Moreover, since drug antibiotics are non-specific with respect to the types of bacteria that they effect, the bacterial flora that naturally occur within the body are killed along with the disease-causing bacterial pathogen. At least 200 identified bacterial species normally inhabit the human body, and many of the these species synthesize and excrete vitamins vital for human health, promote the development of certain tissues, e.g., lymphatic tissue, e.g., Peyer's patches, and stimulate the production of cross-reactive "natural" antibodies that react with pathogenic bacteria. Moreover, natural bacterial flora greatly inhibit colonization by non-indigenous bacteria through normal niche colonization or by producing substances and bacteriocins that can inhibit and kill foreign bacteria. Conventional broad spectrum antibiotics risk killing the non-pathogenic bacteria that are responsible for these beneficial effects.

Bacterial drug resistance was evident at the onset of drug antibiotic therapy, and drug resistant virulent strains of both gram-negative bacteria (including pathogenic strains of *Escheria coli*) and gram-positive bacteria (including pathogenic strains of Staphylococcus and Streptococcus) have become increasingly resistant to drug antibiotics. This increased resistance arises primarily from selection for virulent-resistance strains by the presence of drug antibiotics, resulting in the lateral transfer of resistance genes between different strains and species of bacteria. Epidemic outbreaks have been attributed to a single clone of a benign or virulent progenitor, as well as spontaneous multi-clonal populations within a community setting when drug antibiotic usage is increased. Although decreased usage of antibiotics may improve the odds of generating a population of virulent bacteria that are less resistance towards antibiotics, much contradictory evidence is beginning to surface. For example, a study in Finland found that the incidence of *Streptococcus pyogenes* resistance to macrolide decreased after macrolide treatment was reduced in favor of treatment with erythromycin. However, a follow-up study reported a subsequent 17% increase in *Streptococcus pyogenes* resistance to erythromycin. Another growing concern is the increasing number of multi-resistant bacteria. In 1968 approximately 12,500 people in Guatemala died from an epidemic of Shigella, caused by a bacterial strain that contained a plasmid encoding genes resistant to four different antibiotics (Davies (1996) *Nature* 383:219). Population genetics studies of virulent bacteria causing disease outbreaks or increases in frequency and virulence have shown that the distinct clones responsible for the acute outbreaks are often characterized by unique combinations of virulence genes or alleles of those genes.

Increasing drug antibiotic resistance has resulted in increased dosage levels and duration of antibiotic treatment. These practices are associated with hypersensitivity and serious side effects in a growing number of patients (see Cunha (2001) *Med Clin North Am* 85:149; Kirjavainen and Gibson (1999) *Ann Med* 31:288; Lee et al. (2000) *Arch Intern Med* 160:2819; and Martinez et al. (1999) *Medicine* 78:361). The increasing hypersensitivity and side effects are not being seriously addressed and have so far been clinically under-evaluated (Demoly et al. (2000) *Bull Acad Natl Med* 184:761; and Gruchalla (2000) *Allergy Asthma Proc* 21:39). As an example of one serious side effect that is becoming increasingly prevalent, especially in children, the use of antibiotics has been shown to be positively associated with the development of asthma and atopy. The mechanisms underlying these associations remain largely unknown (von Hertzen (2000) *Ann Med* 32:397).

Drug antibiotics and their effects are not isolated to individuals under the supervision of a doctor's care, but are a communal health issue. Molecular population studies have identified healthy humans that are VRE (vancomycin-resistant enterococci) carriers. An increase in VRE strains in healthy farm animals is associated with the increased use of the antibiotic avoparcin. There is currently a tentative link between the consumption of farm animals and VRE transference to people (Bates (1998) *J Hosp Infect* 27:89). Data on antibiotic resistance profiles of several food born pathogens provides ample evidence that antibiotic resistance traits have entered the microflora of farm animals and the food supply produced from them (Teuber (1999) *Cell Mol Life Sci* 56:755).

SUMMARY

The present invention is based, at least in part, on the development of intracellular peptide toxins and peptide-like toxins that are toxic to a cell when inside the cell, but relatively non-toxic to the cell when outside the cell. Such peptide toxins and peptide-like toxins are useful in the production of a recombinant bacteriophage that effectively function as a bacteriocide (i.e., a toxin-phage bateriocide) that can provide a viable alternative to conventional drug antibiotics. The toxin-phage bacteriocide (TPB) include bacteriophage that have been genetically engineered to encode a peptide toxin that can be expressed within the bacterial host cell. Within the bacterial host cell, the peptide toxin is active and functions to kill the bacterial host cell. Importantly, the toxin-phage bacteriocide of the invention retains its activity as a bacteriophage, and is therefore capable of completing the lytic phase of its lifecycle. Completion of the lytic phase of its life-cycle results in both the production of additional toxin-phage bacteriocide and host cell lysis.

Accordingly, in one aspect, the invention features a method of producing a toxin-phage bacteriocide. The method includes: (a) identifying a bacteriophage that is capable of infecting a bacterial cell of interest; (b) preparing a recombinant bacteriophage genome via the introduction of a nucleic acid sequence that encodes an intracellular peptide toxin into the genome of the bacteriophage, wherein the nucleic acid sequence that encodes the peptide toxin is operatively linked to a promoter that is active within the bacterial cell of interest; and (c) allowing the formation of a toxin-phage bacteriocide particle that contains the recombinant bacteriophage genome.

In preferred embodiments, the nucleic acid sequence that encodes an intracellular peptide toxin includes the nucleic acid of SEQ ID NO: 1, which encodes the TPB peptide toxin A amino acid sequence (SEQ ID NO: 2). In other embodiments, the nucleic acid sequence that encodes an intracellular peptide toxin encodes a peptide toxin other than the TPB peptide toxin A, e.g., a peptide toxin that is a variant of the amino acid sequence of TPB peptide toxin A, or a peptide toxin that functions analogously to the TPB peptide toxin A. In some embodiments, a variant of the TPB peptide toxin A includes at least one mutation, e.g., an insertion, deletion, or point mutation. In preferred embodiments, the mutation is located at one or more of amino acids 16, 17, 18, 19, 20, 21, and 22 of SEQ ID NO: 2. In other preferred embodiments, the mutation is a conservative amino acid substitution. In still other preferred embodiments, the mutation does not change the net ionic charge of the resulting TPB peptide toxin variant, as compared to TPB peptide toxin A, under conditions of physiological pH. The following amino acid substitutions are among those considered conservative:

| For Amino Acid | Code | Replace with any of . . . |
|---|---|---|
| Alanine | Ala | Gly, Cys, Ser |
| Arginine | Arg | Lys, His |
| Asparagine | Asn | Asp, Glu, Gln, |
| Aspartic Acid | Asp | Asn, Glu, Gln |
| Cysteine | Cys | Met, Thr, Ser |
| Glutamine | Gln | Asn, Glu, Asp |
| Glutamic Acid | Glu | Asp, Asn, Gln |
| Glycine | Gly | Ala |
| Histidine | His | Lys, Arg |
| Isoleucine | Ile | Val, Leu, Met |
| Leucine | Leu | Val, Ile, Met |
| Lysine | Lys | Arg, His |
| Methionine | Met | Ile, Leu, Val |
| Phenylalanine | Phe | Tyr, His, Trp |
| Proline | Pro | |
| Serine | Ser | Thr, Cys, Ala |
| Threonine | Thr | Ser, Met, Val |
| Tryptophan | Trp | Phe, Tyr |
| Tyrosine | Tyr | Phe, His |
| Valine | Val | Leu, Ile, Met |

The invention also features a nucleic acid molecule, e.g., an isolated nucleic acid molecule comprising a nucleotide sequence encoding a polypeptide consisting essentially of SEQ ID NO: 2. The invention also includes nucleic acid molecules encoding polypeptides comprising or consisting of SEQ ID NO: 2.

Preferably, the nucleic acid molecule encoding the TPB peptide toxin includes a bacterial promoter and other sequences required to direct transcription and translation of TPB peptide toxin in the bacterial cell being targeted. Those skilled in the art can readily obtain promoter sequences and other sequences required for expression.

In preferred embodiments, homologous recombination is used to introduce the nucleic acid sequence that encodes the intracellular peptide toxin into the bacteriophage genome. In related embodiments, homologous recombination is carried out in vitro. In other related embodiments, homologous recombination is carried out in vivo. In other embodiments, the recombinant bacteriophage genome is packaged into bacteriophage particles in vitro or in vivo, thereby resulting in the production of toxin-phage bacteriocide particles.

In a related aspect, the invention features compositions that include at least one toxin-phage bacteriocide. In preferred embodiments, the toxin phage bacteriocide includes a nucleic acid sequence encoding an intracellular peptide toxin. In particularly preferred embodiments, the toxin phage bacteriocide includes a nucleic acid sequence encoding the TPB peptide toxin A (SEQ ID NO: 2). In other embodiments, the toxin phage bacteriocide includes a nucleic acid sequence encoding TPB peptide toxin A variants.

In preferred embodiments, the compositions include a single strain or multiple variant strains of toxin-phage bacteriocide that has been substantially purified away from the bacterial host cells used to produce or amplify the toxin-phage bacteriocide. In other preferred embodiments, the compositions include a toxin-phage bacteriocide that has been substantially purified away from the bacterial host cell medium in which the bacterial host cells were grown during the production or amplification of the toxin-phage bacteriocide. In other embodiments, the compositions include a toxin-phage bacteriocide that has been partially purified from the bacterial host cells and bacterial host cell medium used to produce or amplify the toxin-phage bacteriocide.

In another aspect, the invention features a method of using a toxin-phage bacteriocide to kill a bacterial cell. The method involves contacting bacterial cells (e.g., bacterial cells that include one ore more strains or species of bacteria) with a toxin-phage bacteriocide, such that at least one toxin-phage is able to bind to and infect at least one bacterial cell, and then allowing the toxin-phage that have infected bacterial cells to kill the bacterial cells. In preferred embodiments, the toxin-phage binds to and infects bacterial cells that are of a selected type. In other preferred embodiments, the toxin-phage does not bind to or infect bacterial cells that are not of the selected type. The contacting can occur within a patient, e.g., a human or animal patient, or in vitro. In vitro studies using the gram negative *Escheria coli* and gram positive *Bacillus subtilus* have found a 100% non-infectivity in the presence of a foreign toxin-phage.

In some embodiments, an infected bacterial cell is killed as a result of the toxin-phage entering into the lytic phase of its life-cycle, such that the bacterial cell is killed by lysis. In other embodiments, the infected bacterial cell is killed as a result of the expression of the toxic peptide encoded by the nucleic acid molecule that was introduced into the genome of the toxin-phage. In still other embodiments, the bacterial cell is killed by a combination of the toxin-phage entering into the lytic phase of its life-cycle and the expression of the toxic peptide encoded by the nucleic acid molecule that was introduced into the bacterial cell by the toxin-phage. In other embodiments, a bacterial cell that is killed is either a gram-negative or a gram-positive bacterial cell.

In another aspect, the invention features a pharmaceutical composition that includes at least one toxin-phage bacteriocide and at least one pharmaceutically acceptable carrier. In preferred embodiments, the pharmaceutical composition can be used in vivo, e.g., the pharmaceutical composition can be administered, e.g., by parenteral injection or orally, to a subject, to treat a bacterial infection present in the subject. In other embodiments, the pharmaceutical composition can be used topically to treat a bacterial infection present in or on a subject.

In another aspect, the invention features a method of using a toxin-phage bacteriocide to treat a bacterial infection present in or on a subject. In some embodiments, the subject is a farm animal, e.g., a chicken, pig, goat, sheep, cow, or horse. In other embodiments the subject is a plant, e.g., an agricultural product or orchard tree. In other embodiments, the subject is a pet, e.g., a fish, bird, cat, or dog. In still other embodiments, the subject is a mammal, a primate, or a human. In preferred embodiments, the toxin-phage bactericide kills the bacteria that are the cause of the infection. In other embodiments, the toxin-phage bactericide slows or brings to a halt the spread of the bacterial infection. In preferred embodiments, the toxin-phage bactericide helps eliminate the bacterial infection. In other preferred embodiments, the toxin-phage bactericide does not kill the bacterial cells that are not the cause of the infection, e.g., bacterial cells that are normally present in the subject or are beneficial to the subject. In other embodiments, the infection constitutes a localized disease, e.g., a disease of the skin, nervous system, cardiovascular system, respiratory system, digestive system, and urinary and reproductive systems.

In another aspect, the invention features a method of using a toxin-phage bacteriocide to prophylactically treat a potential bacterial infection in a subject. In some embodiments, the subject is a farm animal, e.g., a chicken, pig, goat, sheep, cow, or horse. In other embodiments the subject is a plant, e.g., an agricultural product or orchard tree. In other embodiments the subject is a pet, e.g., a fish, bird, cat, or dog. In still other embodiments, the subject is a mammal, a primate, or a human. In preferred embodiments, the toxin-phage bactericide kills the bacteria that are the potential cause of infection. In other embodiments, the toxin-phage slows or brings to a halt the growth of the bacteria that are the potential cause of infection. In other preferred embodiments, the toxin-phage bactericide does not kill bacterial cells that are not the potential cause of infection, e.g., bacterial cells that are normally present in the subject or are beneficial to the subject. In other embodiments, the potential bacterial infection can result in acne, e.g., skin acne in a human. In other embodiments, the subject has an injury, e.g., a cut that breaks the outer dermal layer of the skin, an animal bite, a dermal burn, or a surgical wound or incision, or a surgically inserted device, e.g., a catheter, that is highly susceptible to bacterial infection. In still other embodiments, the potential bacterial infection can involve exposure to biological weapons, e.g., anthrax, plague, or tularemia.

In another aspect, the invention features a method of treating an aqueous solution with a toxin-phage bacteriocide such that bacteria present in the solution are killed. In one embodiment, the resulting aqueous solution is partially sterilized and can subsequently be consumed by an animal, e.g., a farm animal, pet, mammal, primate, or human. Treatment of the aqueous solution will reduce the chance of bacterial infection resulting from consumption of the solution. In another embodiment, the aqueous solution is a solution that is subject to bacterial contamination, e.g., the water in a fish tank or wastewater, e.g., sewage.

In another aspect, the invention features a method of treating a surface with one or more toxin-phage bacteriocides such that bacteria attached to the surface are killed or their growth is inhibited. In one embodiment, the surface is part of a device, e.g., a device that is used in medicine (e.g., surgical instruments), agriculture, industrial processes, or water and wastewater treatment. In another embodiment, the surface is covered with a biofilm. In other embodiments, the surface is treated regularly with a toxin-phage bacteriocide such that the formation of a biofilm is prevented or slowed.

The details of one or more embodiments of the invention are set forth in the accompanying drawings and the description below. Other features, objects, and advantages of the invention will be apparent from the description and drawings, and from the claims.

DETAILED DESCRIPTION

The recombinant toxin-phage bacteriocide (TPB) of the invention is a genetically modified bacteriophage that has been modified to harbor a nucleotide sequence encoding a specialized intracellular peptide toxin. This peptide toxin, e.g., the TPB peptide toxin A, is toxic to cells, e.g., bacterial cells when it is present inside the cell, but not when it is outside of a cell. The TPB allows efficient production of a peptide toxin within cells, thus killing the cells. The TPB of the invention are capable of killing a targeted species of bacteria during both lytic and lysogenic infection. This is in contrast to many therapeutic bacteriophages used previously, which can kill host bacteria only during the lytic phase. The TPB of the invention are species-specific. Therefore, significant numbers of commensal bacterial within the host will not become infected or killed by the TPB. Upon infection the TPB delivers its chromosomal DNA into the bacterial host cell. Lytic toxin-phage reproduction results in additional TPB that burst from the cell and infect additional bacterial host cells. Alternatively, depending on various environmental factors, some TPB infected bacterial cells enter lysogeny, incorporating the TPB chromosomal DNA into their own chromosomal DNA. Upon lysogenization of the bacterial cell, but not limited to this temporal event, the bacterial cell's transcriptional and translational apparatus produces the intracellular peptide toxin. The intracellular peptide toxin, when presented to a cell internally, kills the cell. Upon death of the cell, the intracellular peptide toxin is released into the extracellular environment. However, intracellular peptide toxins are not significantly toxic to cells when presented externally. For example, TPB peptide toxin A had no observable effect on cultures of E. coli or Bacillus Subtilis growing at 37° C. even when present at concentrations as high as 34.6 mM over a 25 hour period. Similarly, TPB peptide toxin A added to cultures of Pichia pastoris yeast cells had no observable effect. Finally, 10 µm TPB peptide toxin A had no observable effect on confluent mouse mammary carcinoma cells growing in EMT6 medium or Hanks Balanced Salt Solution over a 6 hour period.

TPB can be designed to be specific for any selected strain of bacteria, thus desirable bacteria can be spared. Bacteriophage specific for a single bacterial host in nature have been found to remain within the host for as long as the bacterial host specific for that phage is present. Weber-Dabrowska, et al. (1987), *Arch Immunol Ther Exp* (Warsz) 35(5):563–8, tested for absorption of orally administered anti-staphylococcal and anti-pseudomomas phage in both urine and serum samples of patients with suppurative bacterial infections. No phage was present in any of the 56 patients prior to phage therapy. By day 10, 84% of the serum samples and 35% of urine samples contained phage, indicating bioavailability. The healthy control group exhibited a phage titer drop 100-fold between days 0–5. A comprehensive review of phage therapy (Alisky et al. (1998), *J of infection* 36:5) concluded that all studies with both human and animals showed no measurable antiphage antibodies generated.

Without being bound by any particular theory, it appears that the TPB peptide toxin A, produced by a TPB of the invention, becomes introduced into internally available membranes of the cell. This has been observed to occur in both bacterial and yeast cells. In vitro studies using a lipid bilayer membrane model suggest that the toxin peptide permeabilizes membranes. Significantly, the TPB peptide toxin A does not appear to harm either bacterial cells or eukaryotic cells when applied externally, e.g., when introduced in a culture of growing cells.

The TPB peptide toxin A of the invention has also been found to be toxic to eukaryotic cell when presented internally. Thus, intracellular peptide toxins can be used to selectively target undesirable eukaryotic cells, e.g., cancer cells or virally infected cells, by selectively delivering the peptide toxins to the interior of the undesirable cells. Thus, the peptide toxins can be targeted to such cells in various ways, e.g., through receptor mediated targeting.

This invention is further illustrated by the following examples that should not be construed as limiting.

EXAMPLE 1

Production of a Toxin Gene Master Stock

A nucleic acid molecule encoding the TPB peptide toxin A can be prepared synthetically. The molecule has the sequence: ATG GAT TGG CTG AAA GCT CGG GTT GAA CAG GAA CTG CAG GCT CTG GAA GCA CGT GGT ACC GAT TCC AAC GCT GAG CTG CGG GCT ATG GAA GCT AAA CTT AAG GCT GAA ATC CAG AAG (SEQ ID NO: 1). The nucleic acid molecule encodes a 39 amino acid peptide having the sequence: MDWLKARVEQELQALEARGTDSNAEL-RAMEAKLKAEIQK (SEQ ID NO: 2).

The TPB peptide toxin A encoding nucleic acid molecule (SEQ ID NO: 1) was inserted into pET19b plasmid (Novagen, Inc.; Madison, Wis.). The expression vector BL21-Gold(DE3)plysS (Stratagene, Inc.; La Jolla Calif.) was used for expression of the TPB peptide toxin A for in vitro studies. A TPB peptide toxin A encoding gene can be prepared by PCR amplifying a TPB peptide toxin A encoding nucleic acid molecule out of the pET19b plasmid, as discussed below, or by PCR amplification from a synthetically prepared nucleic acid molecule.

The top strand 5' oligonucleotide (SEQ ID NO: 3) used for PCR amplification of the TPB peptide toxin A encoding gene included: an multiple cloning site (MCS), a promoter sequence that is functionally active in both gram-negative and gram-positive bacterial hosts, and a sequence homologous to the 5' start region of the toxin gene sequence. It had the following sequence: GCGTCCGGCGTAGAGGATC-CAAGCTTTAATTTAAATTTTATTTGACAAAAATGGG CTCGTGTTGTACAAATGTATGGATTG-GCTGAAAGCTCGGGTTGAACAGG (SEQ ID NO: 3). The first underlined portion is the MCS sequence. Restriction endonucleases that are capable of cutting within this MCS sequence are shown in Table I.

TABLE I

| Enzyme | No. | Position | Sequence |
| --- | --- | --- | --- |
| AclWI | 1 | 19 | ggatc |
| AluI | 1 | 23 | ag/ct |
| AlwI | 1 | 19 | ggatc |
| BamHI | 1 | 15 | g/gatcc |
| BsiSI | 1 | 5 | c/cgg |
| Bsp143I | 1 | 15 | /gatc |
| BstI | 1 | 15 | g/gatcc |
| BstX2I | 1 | 15 | r/gatcy |
| BstYI | 1 | 15 | r/gatcy |
| CviJI | 1 | 23 | rg/cy |
| DpnI | 1 | 17 | ga/tc |
| DpnII | 1 | 15 | /gatc |
| HapII | 1 | 5 | c/cgg |
| HgaI | 1 | 5 | gacgc |
| HindIII | 1 | 21 | a/agctt |
| HpaII | 1 | 5 | c/cgg |
| Kzo9I | 1 | 15 | /gatc |
| MboI | 1 | 15 | /gatc |
| MflI | 1 | 15 | r/gatcy |
| MnlI | 1 | 16 | cctc |
| MseI | 1 | 26 | t/taa |
| MspI | 1 | 5 | c/cgg |
| NdeII | 1 | 15 | /gatc |
| NlaIV | 1 | 17 | ggn/ncc |
| PspN4I | 1 | 17 | ggn/ncc |
| Sau3AI | 1 | 15 | /gatc |
| Sse9I | 1 | 27 | /aatt |
| Tru1I | 1 | 26 | t/taa |
| Tru9I | 1 | 26 | t/taa |
| Tsp509I | 1 | 27 | /aatt |
| TspEI | 1 | 27 | /aatt |
| XhoII | 1 | 15 | r/gatcy |

The central portion of the top strand 5' oligonucleotide sequence (SEQ ID NO: 3), which is not underlined, constitutes the VegI/II promoter sequence. The VegI/II promoter sequence has been shown by Pescheke et al. (1985), *J Mol Biol* 186:547, to be active in both gram-negative and gram-positive bacterial cells. The second underlined portion of the top strand 5' oligonucleotide sequence corresponds to the 5' end of the TPB peptide toxin A gene sequence (SEQ ID NO :1). This sequence is capable of annealing to the bottom strand of the pET19b plasmid, e.g., in a PCR reaction.

The bottom strand 3' oligonucleotide (SEQ ID NO: 4) used for PCR amplification of the TPB peptide toxin A encoding gene included a MCS site and a sequence complementary to the 3' end of the toxin gene sequence. The terminator region present in the pET19b vector was not amplified so that the functional properties of the toxin peptide could be disrupted, rendering the gene product less toxic to the master stock host cell. The bottom strand 3' oligonucleotide used for PCR amplification had the sequence: CCATCGATGGCCGCTCGAGCTAT-TATTTCTGGATTTCAG (SEQ ID NO: 4). The underlined portion of SEQ ID NO: 4 constitutes the multiple cloning sites (MCS) sequence Restriction endonucleases that are capable of cutting within this MCS sequence are shown in Table II.

TABLE II

| Enzyme | # | Position | Sequence |
|---|---|---|---|
| AccBSI | 1 | 16 | gagcgg |
| AciI | 1 | 14 | ccgc |
| Ama87I | 1 | 14 | c/ycgrg |
| AvaI | 1 | 14 | c/ycgrg |
| BanIII | 1 | 4 | at/cgat |
| BcoI | 1 | 14 | c/ycgrg |
| Bsa29I | 1 | 4 | at/cgat |
| BscI | 1 | 4 | at/cgat |
| BseCI | 1 | 4 | at/cgat |
| BsoBI | 1 | 14 | c/ycgrg |
| BsoFI | 1 | 11 | gc/ngc |
| Bsp106I | 1 | 4 | at/cgat |
| BspDI | 1 | 4 | at/cgat |
| BspXI | 1 | 4 | at/cgat |
| BsrBI | 1 | 6 | gagcgg |
| BstD102I | 1 | 16 | gagcgg |
| Bsu15I | 1 | 4 | at/cgat |
| BsuRI | 1 | 10 | gg/cc |
| CfrI | 1 | 8 | y/ggccr |
| ClaI | 1 | 4 | at/cgat |
| CviJI | 1 | 10 | rg/cy |
| EaeI | 1 | 8 | y/ggccr |
| Eco88I | 1 | 14 | c/ycgrg |
| Fsp4HI | 1 | 11 | gc/ngc |
| HaeIII | 1 | 10 | gg/cc |
| ItaI | 1 | 11 | gc/ngc |
| PaeR7I | 1 | 14 | c/tcgag |
| PalI | 1 | 10 | gg/cc |
| Sfr274I | 1 | 14 | c/tcgag |
| TaqI | 2 | 4, 15 | t/cga |
| TthHB8I | 2 | 4, 15 | t/cga |
| XhoI | 1 | 14 | c/tcgag |

The portion of the bottom strand 3' oligonucleotide sequence that is not underlined is complementary to the 3' end of the TPB peptide toxin A encoding gene sequence. This complementary sequence is capable of annealing to the top strand of the pET19b plasmid, e.g., in a PCR reaction.

Following PCR amplification of the TPB peptide toxin A encoding gene using the top strand 5' and the bottom strand 3' oligonucleotides described above, the PCR product was gel purified (Qiagen, QIAquick Gel Extraction Kit, Cat.No.28704) and sequenced (by Research Genetics). Oligonucleotide primers used for sequencing included: GGCG-TATCACGAGGCCC (SEQ ID NO: 5); and GTGGCGC-CGGTGATGCCGG (SEQ ID NO: 6). SEQ ID NO: 5 was used to sequence the PCR product from the 5' direction, while SEQ ID NO: 6 was used to sequence the PCR product from the 3' direction.

The purified PCR product was cut with the restriction endonucleases ClaI and BamHI and ligated into a pBR322 plasmid (ATCC 37017, 31344) that had been cut with the same enzymes. Insertion of the PCR product containing the TPB peptide toxin A gene PCR product into the pBR322 plasmid disrupted the tetR gene, negating tetracycline resistance. This disruption, in turn, allowed for a positive gene incorporation selection tool. Once a positive clone was identified, the region of the plasmid containing the TPB peptide toxin A gene PCR product was analyzed using restriction digests, and then sequenced.

The resulting plasmid was transformed into competent HB101 (MAX Efficiency HB101 Competent Cells, Cat. No. 18296-012, Life Technologies), and a positive clone was chosen using ampicillin resistance as a selection criteria. A single colony clone was selected and cultured to exponential growth phase (LB, 37° C., 250 rpms), mixed with sterile glycerol (80:20 ratio) and stored in a −76° C. freezer.

EXAMPLE 2

Selection of Toxin Gene Integration Sites

Both a gram-negative and a gram-positive bacterial species with their complimentary bacteriophages were chosen to illustrate the effectiveness of TPB peptide toxin A.

*Escherichia coli* (c600, ATCC Accession No. 23724) was chosen as an example of a gram-negative bacterial species that could be tested for the effects of a toxin-phage bacteriocide. There are many bacteriophage that are known to infect *E. coli*, one of which is lambda phage (ATCC Accession No. 23724-B2). The sequence of the lambda phage genome is described in Sanger et al. (1992) *J Mol Biol* 162:729, the contents of which are incorporated herein by reference. The integration site for the TPB peptide toxin gene into the lambda phage genome was chosen to be between nucleotides 46,468 and 46,469. The nucleotide sequences of the regions immediately surrounding the chosen integration site are as follows: TTGCCCATATC-GATGGGCAACTCATGCAATTATTGTGAG (SEQ ID NO: 7); and CAATACACACGCGCTTCCAGCGGAG-TATAAATGCCTAAAGTA (SEQ ID NO: 8). SEQ ID NO: 7 corresponds to the nucleotide sequence that is 5' to the integration site, about nucleotides 46,430–46,468 of the lambda phage genome, while SEQ ID NO: 8 corresponds to the nucleotide sequence that is 3' to the integration site, about nucleotides 46,469–46,510 of the lambda phage genome.

*Bacillus subtilis* (BGSC #1L32, BGSC, Ohio State University, Columbus, Ohio) was chosen as an example of a gram-positive bacterial species that could be tested for the effects of a toxin-phage bacteriocide. There are many bacteriophage that are known to infect *B. subtilis*, one of which is phi-105 (BGSC #1A304(phi-105), BGSC, Ohio State University, Columbus, Ohio). The sequence of the phi-105 genome is available from the NCBI database on the Internet at ncbi.nim.nih.gov/entrez/query.fcgi. The integration site for the TPB peptide toxin gene into the phi-105 genome was chosen to be between nucleotides 38,448 and 38,449. The nucleotide sequences of the regions immediately surrounding the chosen integration site are as follows: GGGTAGT-TGCATACCACTAAAGATGTTCAGGTGCACATG (SEQ ID NO: 9); and AGCATTGGAGGAAAGGAACGCTT-TAGGGGGAAGGGAAACC (SEQ ID NO: 10). SEQ ID NO: 9 corresponds to the nucleotide sequence that is 5' to the integration site, about nucleotides 38,409–38,448 of the phi-105 genome, while SEQ ID NO: 10 corresponds to the nucleotide sequence that is 3' to the integration site, about nucleotides 38,449–38,488 of the phi-105 genome.

EXAMPLE 3

Introduction of a 3' Terminator Sequence

Before introducing the TPB peptide toxin A gene into the bacteriophage genomes, a terminator sequence can be added to the 3' end of the toxin gene in order increase the stability of toxin gene RNA synthesized within the bacterial host cell. Addition of a terminator sequence to the 3' end of the toxin gene can be accomplished by PCR, as it was in this example, as well as by other techniques known in the art, e.g., restriction fragment subcloning.

The top strand 5' oligonucleotide (SEQ ID NO: 12) used to introduce the terminator sequence included the MCS sequences (SEQ ID NO: 13) and a portion of the VegI/II promoter described in Example 1. The bottom strand 3' oligonucleotide (SEQ ID NO: 13) used to introduce the terminator sequence included a MCS sequence distinct from the MCS sequences described in Example 1, a 3' terminator sequence, and a sequence complementary to the 3' end of the TPB peptide toxin A gene.

The top strand 5' oligonucleotide used to add the terminator sequence to the TPB peptide toxin A gene had the sequence: CGTCCGGCGTAGAGGATCCAAGCTT-TAATTTAAATTTT (SEQ ID NO: 11). The underlined portion of the top strand 5' oligonucleotide sequence constitutes the MCS sequence. The multiple cloning sites sequence was introduced to allow versatility in manipulation of the PCR products and possible associated vectors. Restriction endonucleases that are capable of cutting within this MCS sequence are shown in Table I. The portion of the top strand 5' oligonucleotide sequence that is not underlined corresponds to a portion of the VegI/II bacterial promoter added to the 5' end of the TPB peptide toxin A gene produced in Example 1. The entire sequence of the top strand 5' oligonucleotide sequence (SEQ ID NO: 11) is capable of annealing to the TPB peptide toxin A gene construct produced in Example 1.

The bottom strand 3' oligonucleotide used to add the terminator sequence to the TPB peptide toxin A gene had the sequence: CGGGAAGCTTGGATCCGCATAG-CAAAACGGACATCACTCCGTTTCAATGGAGGT GATGTCCGTTTTCCGCTCGAGCTAT-TATTTCTGGATTTCAGC (SEQ ID NO: 12). The first underlined portion of the bottom strand 3' oligonucleotide sequence constitutes the MCS sequence. Restriction endonucleases that are capable of cutting within this MCS sequence are shown in Table III.

TABLE III

| Enzyme | # | Position | Sequence |
|---|---|---|---|
| AciI | 1 | 18 | ccgc |
| AclWI | 1 | 15 | ggatc |
| AluI | 1 | 7 | ag/ct |
| AlwI | 1 | 15 | ggatc |
| BamHI | 1 | 11 | g/gatcc |
| Bsp143I | 1 | 11 | /gatc |
| BstI | 1 | 11 | g/gatcc |
| BstX2I | 1 | 11 | r/gatcy |
| BstYI | 1 | 11 | r/gatcy |
| CviJI | 1 | 7 | rg/cy |
| DpnI | 1 | 13 | ga/tc |
| DpnII | 1 | 11 | /gatc |
| HindIII | 1 | 5 | a/agctt |
| Kzo9I | 1 | 11 | /gatc |
| MboI | 1 | 11 | /gatc |
| MflI | 1 | 11 | r/gatcy |
| NdeII | 1 | 11 | /gatc |
| NlaIV | 1 | 13 | ggn/ncc |
| PspN4I | 1 | 13 | ggn/ncc |
| Sau3AI | 1 | 11 | /gatc |
| XhoII | 1 | 11 | r/gatcy |

The central portion of the bottom strand 3' oligonucleotide sequence (SEQ ID NO: 12), which is not underlined above, is the 3' terminator sequence complement. The corresponding 3' terminator sequence has been shown to form a stem-loop structure that is a positive retroregulator that stabilizes mRNAs in bacteria. This 3' terminator sequence has been described in Wong and Chang (1986) Proc Natl Acad Sci USA 83:3233. The second underlined portion of the bottom strand 3' oligonucleotide sequence is the complement of the 3' end of the TPB peptide toxin A gene sequence (SEQ ID NO: 1). This sequence is capable of annealing to the bottom strand of the TPB peptide toxin A gene master stock plasmid produced in Example 1, e.g., in a PCR reaction.

DNA isolated from the toxin gene bacterial stock produced in Example 1 was used as template for the PCR reaction involving the top strand 5' and bottom strand 3' oligonucleotides described above (SEQ ID NOS: 11 and 12, respectively). Following PCR, the amplified TPB peptide toxin A gene containing the 3' terminator sequence was gel purified (Qiagen, QIAquick Gel Extraction Kit, Cat.No.28704), analyzed by endonuclease restriction fragment analysis, and used in Example 4.

EXAMPLE 4

Recombinageneic Bacteriophage-Integrating Intracellular Peptide Toxin Genes

Generation of toxin genes recombinagenic with a phage genome can be produced by introducing phage genomic sequences located 5' and 3' to a chosen integration site in the phage genome to the 5' and 3' ends, respectively, of a intracellular peptide toxin encoding gene.

Generation of toxin genes recombinagenic with the lambda phage genome were produced by the addition of lambda phage genomic sequences located 5' (SEQ ID NO: 7) and 3' (SEQ ID NO: 8) to the chosen integration site (see Example 2) to the 5' and 3' ends, respectively, of the TPB peptide toxin A gene produced in Example 3. A single round of PCR was used to make the additions. The primers used in the PCR reaction included a 5' Lambda Oligonucleotide (SEQ ID NO: 13), consisting of a MCS sequence, a 5' homologous recombination sequence, a HindIII restriction site sequence, and a 5' annealing sequence, and a 3' Lambda Oligonucleotide (SEQ ID NO: 14), consisting of a MCS sequence, a 3' homologous recombination sequence, a second MCS sequence, and a 3' annealing sequence.

The 5' Lambda Oligonucleotide had the sequence: CCG-GAATTCGCTAGCGGGCCCGAGTTGC-CCATATCGATGGGCAACTCATGCAAT TATTGT-GAGAAGCTTTAATTTAAATTTTATTTGACAAAAA TGGG (SEQ ID NO: 13). The first underlined portion of the 5' Lambda Oligonucleotide sequence constitutes MCS sequence. The MCS was introduced so that it would be easier to manipulate the PCR product for possible cloning into alternative vectors. Alternatively, the MCS region allows one to determine whether the toxin gene had integrated into the desired location in the lambda phage genome. Integration events that retain this MCS are not likely to have occurred in the desired location and can be discarded, whereas integration events that occurred via homologous recombination are likely to lack this MCS. Alternatively, the homologous recombinant sequence can be PCR amplified without the MCS and introduced into the phage genome. Restriction endonucleases that are capable of cutting within this MCS sequence are shown in Table IV.

TABLE IV

| Enzyme | # | Position | Sequence |
|---|---|---|---|
| AciI | 1 | 17 | ccgc |
| AcsI | 1 | 4 | r/aatty |
| Ama87I | 1 | 19 | c/ycgrg |
| ApaI | 1 | 20 | gggcc/c |
| ApoI | 1 | 4 | r/aatty |
| AspS9I | 1 | 16 | g/gncc |
| AsuI | 1 | 16 | g/gncc |
| AvaI | 1 | 19 | c/ycgrg |
| BanII | 1 | 20 | grgcy/c |
| BcoI | 1 | 19 | c/ycgrg |
| BfaI | 1 | 11 | c/tag |
| BmyI | 1 | 20 | gdgch/c |
| BsiSI | 1 | 1 | c/cgg |
| BsoBI | 1 | 19 | c/ycgrg |
| Bsp120I | 1 | 16 | g/ggccc |
| Bsp1286I | 1 | 20 | gdgch/c |
| BsuRI | 1 | 18 | gg/cc |
| Cac8I | 1 | 12 | gcn/ngc |
| Cfr13I | 1 | 16 | g/gncc |
| CviJI | 1 | 18 | rg/cy |
| Eco24I | 1 | 20 | grgcy/c |
| Eco88I | 1 | 19 | c/ycgrg |
| EcoRI | 1 | 4 | g/aattc |
| FauI | 1 | 18 | cccgc |
| FriOI | 1 | 20 | grgcy/c |
| HaeIII | 1 | 18 | gg/cc |
| HapII | 1 | 1 | c/cgg |
| HpaII | 1 | 1 | c/cgg |
| MaeI | 1 | 11 | c/tag |
| MspI | 1 | 1 | c/cgg |
| NheI | 1 | 10 | g/ctagc |
| NlaIV | 1 | 18 | ggn/ncc |
| PalI | 1 | 18 | gg/cc |
| PspN4I | 1 | 18 | ggn/ncc |
| PspOMI | 1 | 16 | g/ggccc |
| PstNHI | 1 | 10 | g/ctagc |
| Sau96I | 1 | 16 | g/gncc |
| SduI | 1 | 20 | gdgch/c |
| Sse9I | 1 | 4 | /aatt |
| Tsp509I | 1 | 4 | /aatt |
| TspEI | 1 | 4 | /aatt |

The first portion of the 5' Lambda Oligonucleotide (that is not underlined) constitutes the 5' homologous recombination sequence, which was identified in Example 2 as the lambda phage sequence 5' to the integration site. The second underlined portion of the 5' Lambda Oligonucleotide constitutes a Hind III restriction site. Successful targeting of the toxin gene to the chosen site in the lambda phage genome will also result in the introduction of a new Hind III restriction site into the genome at the chosen site. Thus, restriction digest analysis of targeted lambda clones can help assess whether the targeting was successful and whether the toxin gene that has been introduced is intact, i.e., lacks deletions, rearrangements, etc. The second portion of the 5' Lambda Oligonucleotide that is not underlined constitutes the 5' annealing region, which is homologous to a portion of the VegI/I1 promoter sequence located at the 5' end of the PCR product produced in Example 3. This sequence is designed to anneal to the PCR product of Example 3, thereby allowing PCR amplification of a toxin gene that contains lambda phage targeting sequences.

The 3' Lambda Oligonucleotide had the sequence: CGC-CCTAGGCGGCCGAGGACCCTACTTTAG-GCATTTATACTCCGCTGGAAGCGC GTGTGTATTG-GCATGCATCGATTAGTAAAACGGACATCACTCCG (SEQ ID NO: 14). The first underlined portion of the 3' Lambda Oligonucleotide sequence constitutes the first MCS sequence. The MCS was introduced so that it would be easier to manipulate the PCR product for possible cloning into alternative vectors. In addition, this multiple cloning sites sequence was introduced so that it would be easier to determine whether the toxin gene had integrated into the desired location in the lambda phage genome. Integration events that retain this MCS are not likely to have occurred in the desired location and can be discarded, whereas integration events that occurred via homologous recombination are likely to lack this MCS. Alternatively, the homologous recombinant sequence can be PCR amplified without the MCS and introduced into the phage genome. Restriction endonucleases that are capable of cutting within this MCS sequence are shown in Table V.

TABLE V

| Enzyme | # | Position | Sequence |
|---|---|---|---|
| AciI | 1 | 12 | ccgc |
| AspS9I | 1 | 17 | g/gncc |
| AsuI | 1 | 17 | g/gncc |
| AvaII | 1 | 17 | g/gwcc |
| AvrII | 1 | 4 | c/ctagg |
| BfaI | 1 | 5 | c/tag |
| BlnI | 1 | 4 | c/ctagg |
| Bme18I | 1 | 17 | g/gwcc |
| BsaJI | 2 | 4, 13 | c/cnngg |
| BsaOI | 1 | 13 | cgry/cg |
| BseDI | 2 | 4, 13 | c/cnngg |
| Bsh1285I | 1 | 13 | cgry/cg |
| BsiEI | 1 | 13 | cgry/cg |
| BsoFI | 1 | 10 | gc/ngc |
| BssT1I | 1 | 4 | c/cwwgg |
| BstMCI | 1 | 13 | cgry/cg |
| BstZI | 1 | 10 | c/ggccg |
| BsuRI | 1 | 12 | gg/cc |
| Cfr13I | 1 | 17 | g/gncc |
| CfrI | 1 | 10 | y/ggccr |
| CviJI | 1 | 12 | rg/cy |
| DraII | 1 | 17 | rg/gnccy |
| EaeI | 1 | 10 | y/ggccr |
| EagI | 1 | 10 | c/ggccg |
| EclXI | 1 | 10 | c/ggccg |
| Eco130I | 1 | 4 | c/cwwgg |
| Eco47I | 1 | 17 | g/gwcc |
| Eco52I | 1 | 10 | c/ggccg |
| EcoO109I | 1 | 17 | rg/gnccy |
| EcoT14I | 1 | 4 | c/cwwgg |
| ErhI | 1 | 4 | c/cwwgg |
| Fsp4HI | 1 | 10 | gc/ngc |
| HaeIII | 1 | 12 | gg/cc |
| HgiEI | 1 | 17 | g/gwcc |
| ItaI | 1 | 10 | gc/ngc |
| MaeI | 1 | 5 | c/tag |
| MnlI | 1 | 18 | cctc |
| NlaIV | 1 | 19 | ggn/ncc |
| PalI | 1 | 12 | gg/cc |
| PpuMI | 1 | 17 | rg/gwccy |
| Psp5II | 1 | 17 | rg/gwccy |
| PspN4I | 1 | 19 | ggn/ncc |
| Sau96I | 1 | 17 | g/gncc |
| SinI | 1 | 17 | g/gwcc |
| StyI | 1 | 4 | c/cwwgg |
| XmaIII | 1 | 10 | c/ggccg |

The first portion of the 3' Lambda Oligonucleotide that is not underlined constitutes the 3' homologous recombination sequence, which was identified in Example 2 as the lambda phage sequence 3' to the integration site. The second underlined portion of the 3' Lambda Oligonucleotide constitutes a second MCS sequence. Successful targeting of the toxin gene to the chosen site in the lambda phage genome will also result in the introduction of the restriction sites present in this MCS into the genome at the chosen site. Thus, restriction digest analysis of targeted lambda clones can help assess whether the targeting was successful and whether the toxin gene that has been introduced is intact, i.e., lacks deletions, rearrangements, etc. Restriction endonucleases that are capable of cutting within this MCS sequence are shown in Table VI.

TABLE VI

| Enzyme | # | Position | Sequence |
|---|---|---|---|
| BanIII | 1 | 9 | at/cgat |
| BbuI | 1 | 6 | gcatg/c |
| Bsa29I | 1 | 9 | at/cgat |
| BscI | 1 | 9 | at/cgat |
| BseCI | 1 | 9 | at/cgat |
| Bsp106I | 1 | 9 | at/cgat |
| BspDI | 1 | 9 | at/cgat |
| BspXI | 1 | 9 | at/cgat |
| Bsu15I | 1 | 9 | at/cgat |
| Cac8I | 1 | 4 | gcn/ngc |
| ClaI | 1 | 9 | at/cgat |
| EcoT22I | 1 | 8 | atgca/t |
| Hsp92II | 1 | 6 | catg/ |
| Mph1103I | 1 | 8 | atgca/t |
| NlaIII | 1 | 6 | catg/ |
| NsiI | 1 | 8 | atgca/t |
| NspI | 1 | 6 | rcatg/y |
| PaeI | 1 | 6 | gcatg/c |
| Ppu10I | 1 | 4 | a/tgcat |
| SfaNI | 1 | 10 | gcatc |
| SphI | 1 | 6 | gcatg/c |
| TaqI | 1 | 9 | t/cga |
| TthHB8I | 1 | 9 | t/cga |
| Zsp2I | 1 | 8 | atgca/t |

The second portion of the 3' Lambda Oligonucleotide (SEQ ID NO: 25) that is not underlined constitutes the 5' annealing region (SEQ ID NO: 28), which is complementary to a portion of the 3' terminator sequence located at the 3' end of the PCR product produced in Example 3. This sequence is designed to anneal to the PCR product of Example 3, thereby allowing PCR amplification of a TPB peptide toxin A gene that contains lambda phage targeting sequences.

Generation of toxin genes recombinagenic with the phi-105 phage genome were produced by the addition of phi-105 phage genomic sequences located 5' (SEQ ID NO: 9) and 3' (SEQ ID NO: 10) to the chosen integration site (see Example 2) to the 5' and 3' ends, respectively, of the TPB peptide toxin A gene produced in Example 3. A single round of PCR was used to make the additions. The primers used in the PCR reaction included a 5' Phi-105 Oligonucleotide (SEQ ID NO: 15), consisting of a MCS sequence, a 5' homologous recombination sequence, a HindIII restriction site sequence, and a 5' annealing sequence, and a 3' Phi-105 Oligonucleotide (SEQ ID NO: 16), consisting of a MCS sequence, a 3' homologous recombination sequence, a second MCS sequence, and a 3' annealing sequence.

The 5' Phi-105 Oligonucleotide had the sequence: CCGGAATTCGCTAGCGGGCCCGAGGGGTAGTTGCATACCACTAAAGATGTTCAG GTGCACATGAAGCTTTAATTTAAATTTTATTTGACAAAAATGGG (SEQ ID NO: 15). The first underlined portion of the 5' Phi-105 Oligonucleotide sequence constitutes the MCS sequence. The multiple cloning sites sequence was introduced so that it would be easier to manipulate the PCR product for possible cloning into alternative vectors. In addition, the MCS region allows one to-determine whether the toxin gene had integrated into the desired location in the lambda phage genome. Integration events that retain this MCS are not likely to have occurred in the desired location and can be discarded, whereas integration events that occurred via homologous recombination are likely to lack this MCS. Alternatively, the homologous recombinant sequence can be PCR amplified without the MCS and introduced into the phage genome. Restriction endonucleases that are capable of cutting within this MCS sequence are shown in Table VII.

TABLE VII

| Enzyme | # | Position | Sequence |
|---|---|---|---|
| AciI | 1 | 17 | ccgc |
| AcsI | 1 | 4 | r/aatty |
| Ama87I | 1 | 19 | c/ycgrg |
| ApaI | 1 | 20 | gggcc/c |
| ApoI | 1 | 4 | r/aatty |
| AspS9I | 1 | 16 | g/gncc |
| AsuI | 1 | 16 | g/gncc |
| AvaI | 1 | 19 | c/ycgrg |
| BanII | 1 | 20 | grgcy/c |
| BcoI | 1 | 19 | c/ycgrg |
| BfaI | 1 | 11 | c/tag |
| BmyI | 1 | 20 | gdgch/c |
| BsiSI | 1 | 1 | c/cgg |
| BsoBI | 1 | 19 | c/ycgrg |
| Bsp120I | 1 | 16 | g/ggccc |
| Bsp1286I | 1 | 20 | gdgch/c |
| BsuRI | 1 | 18 | gg/cc |
| Cac8I | 1 | 12 | gcn/ngc |
| Cfr13I | 1 | 16 | g/gncc |
| CviJI | 1 | 18 | rg/cy |
| Eco24I | 1 | 20 | grgcy/c |
| Eco88I | 1 | 19 | c/ycgrg |
| EcoRI | 1 | 4 | g/aattc |
| FauI | 1 | 18 | cccgc |
| FriOI | 1 | 20 | grgcy/c |
| HaeIII | 1 | 18 | gg/cc |
| HapII | 1 | 1 | c/cgg |
| HpaII | 1 | 1 | c/cgg |
| MaeI | 1 | 11 | c/tag |
| MspI | 1 | 1 | c/cgg |
| NheI | 1 | 10 | g/ctagc |
| NlaIV | 1 | 18 | ggn/ncc |
| PalI | 1 | 18 | gg/cc |
| PspN4I | 1 | 18 | ggn/ncc |
| PspOMI | 1 | 16 | g/ggccc |
| PstNHI | 1 | 10 | g/ctagc |
| Sau96I | 1 | 16 | g/gncc |
| SduI | 1 | 20 | gdgch/c |
| Sse9I | 1 | 4 | /aatt |
| Tsp509I | 1 | 4 | /aatt |
| TspEI | 1 | 4 | /aatt |

The first portion of the 5' Phi-105 Oligonucleotide that is not underlined constitutes the 5' homologous recombination sequence, which was identified in Example 2 as the phi-105 phage sequence 5' to the integration site. The second underlined portion of the 5' Phi-105 Oligonucleotide constitutes a Hind III restriction site. Successful targeting of the toxin gene to the chosen site in the phi-105 phage genome will also result in the introduction of a new Hind III restriction site into the genome at the chosen site. Thus, restriction digest analysis of targeted phi-105 clones can help assess whether the targeting was successful and whether the toxin gene that has been introduced is intact, i.e., lacks deletions, rearrangements, etc. The second portion of the 5' Phi-105 Oligonucleotide that is not underlined constitutes the 5' annealing region, which is homologous to a portion of the VegI/II promoter sequence located at the 5' end of the PCR product produced in Example 3. This sequence is designed to anneal to the PCR product of Example 3, thereby allowing PCR amplification of a toxin gene that contains phi-105 phage targeting sequences.

The 3' Phi-1 05 Oligonucleotide had the following sequence: CGCCCTAGGCGGCCGAGGACCCGGTTTCCCTTCCCCCTAAAGCGTTCCTTTCCTC CAATGCTGGCATGCATCGATTAGTAAAACGGACATCACTCCG (SEQ ID NO: 16). The first underlined portion of the 3' Phi-105 Oligonucleotide sequence constitutes the first MCS sequence. This multiple cloning site sequence was introduced so that it would be easier to manipulate the PCR product for possible cloning into alternative vectors. In addition, it would be easier to determine whether the toxin gene had integrated into the desired location in the lambda phage genome. Integration events that retain this MCS are not likely to have occurred in the desired location and can be discarded, whereas integration events that occurred via homologous recombination are likely to lack this MCS. Alternatively, the homologous recombinant sequence can be PCR amplified without the MCS and introduced into the phage genome. Restriction endonucleases that are capable of cutting within this MCS sequence are shown in Table VIII.

TABLE VIII

| Enzyme | # | Position | Sequence |
|---|---|---|---|
| AciI | 1 | 12 | ccgc |
| AspS9I | 1 | 17 | g/gncc |
| AsuI | 1 | 17 | g/gncc |
| AvaII | 1 | 17 | g/gwcc |
| AvrII | 1 | 4 | c/ctagg |
| BfaI | 1 | 5 | c/tag |
| BlnI | 1 | 4 | c/ctagg |
| Bme18I | 1 | 17 | g/gwcc |
| BsaJI | 2 | 4, 13 | c/cnngg |
| BsaOI | 1 | 13 | cgry/cg |
| BseDI | 2 | 4, 13 | c/cnngg |
| Bsh1285I | 1 | 13 | cgry/cg |
| BsiEI | 1 | 13 | cgry/cg |
| BsoFI | 1 | 10 | gc/ngc |
| BssT1I | 1 | 4 | c/cwwgg |
| BstMCI | 1 | 13 | cgry/cg |
| BstZI | 1 | 10 | c/ggccg |
| BsuRI | 1 | 12 | gg/cc |
| Cfr13I | 1 | 17 | g/gncc |
| CfrI | 1 | 10 | y/ggccr |
| CviJI | 1 | 12 | rg/cy |
| DraII | 1 | 17 | rg/gnccy |
| EaeI | 1 | 10 | y/ggccr |
| EagI | 1 | 10 | c/ggccg |
| EclXI | 1 | 10 | c/ggccg |
| Eco130I | 1 | 4 | c/cwwgg |
| Eco47I | 1 | 17 | g/gwcc |
| Eco52I | 1 | 10 | c/ggccg |
| EcoO109I | 1 | 17 | rg/gnccy |
| EcoT14 | 1 | 4 | c/cwwgg |
| ErhI | 1 | 4 | c/cwwgg |
| Fsp4HI | 1 | 10 | gc/ngc |
| HaeIII | 1 | 12 | gg/cc |
| HgiEI | 1 | 17 | g/gwcc |
| ItaI | 1 | 10 | gc/ngc |
| MaeI | 1 | 5 | c/tag |
| MnlI | 1 | 18 | cctc |
| NlaIV | 1 | 19 | ggn/ncc |
| PalI | 1 | 12 | gg/cc |
| PpuMI | 1 | 17 | rg/gwccy |
| Psp5II | 1 | 17 | rg/gwccy |
| PspN4I | 1 | 19 | ggn/ncc |
| Sau96I | 1 | 17 | g/gncc |
| SinI | 1 | 17 | g/gwcc |
| StyI | 1 | 4 | c/cwwgg |
| XmaIII | 1 | 10 | c/ggccg |

The first portion of the 3' Phi-105 Oligonucleotide that is not underlined constitutes the 3' homologous recombination sequence, which was identified in Example 2 as the phi-105 phage sequence 3' to the integration site. The second underlined portion of the 3' Phi-105 Oligonucleotide constitutes a second MCS sequence. Successful targeting of the toxin gene to the chosen site in the phi-105 phage genome will also result in the introduction of the restriction sites present in this MCS into the genome at the chosen site. Thus, restriction digest analysis of targeted phi-105 clones can help assess whether the targeting was successful and whether the toxin gene that has been introduced is intact, i.e., lacks deletions, rearrangements, etc. Restriction endonucleases that are capable of cutting within this MCS sequence are shown in Table IX.

TABLE IX

| Enzyme | # | Position | Sequence |
|---|---|---|---|
| BanIII | 1 | 9 | at/cgat |
| BbuI | 1 | 6 | gcatg/c |
| Bsa29I | 1 | 9 | at/cgat |
| BscI | 1 | 9 | at/cgat |
| BseCI | 1 | 9 | at/cgat |
| Bsp106I | 1 | 9 | at/cgat |
| BspDI | 1 | 9 | at/cgat |
| BspXI | 1 | 9 | at/cgat |
| Bsu15I | 1 | 9 | at/cgat |
| Cac8I | 1 | 4 | gcn/ngc |
| ClaI | 1 | 9 | at/cgat |
| EcoT22I | 1 | 8 | atgca/t |
| Hsp92II | 1 | 6 | catg/ |
| Mph1103I | 1 | 8 | atgca/t |
| NlaIII | 1 | 6 | catg/ |
| NsiI | 1 | 8 | atgca/t |
| NspI | 1 | 6 | rcatg/y |
| PaeI | 1 | 6 | gcatg/c |
| Ppu10I | 1 | 4 | a/tgcat |
| SfaNI | 1 | 10 | gcatc |
| SphI | 1 | 6 | gcatg/c |
| TaqI | 1 | 9 | t/cga |
| TthHB8I | 1 | 9 | t/cga |
| Zsp2I | 1 | 8 | atgca/t |

The second portion of the 3' Phi-105 Oligonucleotide that is not underlined constitutes the 5' annealing region, which is complementary to a portion of the 3' terminator sequence located at the 3' end of the PCR product produced in Example 3. This sequence is designed to anneal to the PCR product of Example 3, thereby allowing PCR amplification of a TPB peptide toxin A gene that contains phi-105 phage targeting sequences.

EXAMPLE 5

In Vitro Homologous Recombination of an Intracellular Peptide Toxin Gene into a Bacteriophage Genome The homologous recombination event can be manipulated in vitro using isolated bacteriophage DNA added to a bacterial host cell supernatant seeded with the homologous recombination competent PCR product containing a intracellular toxin gene, using the basic protocols as described by Mackal, et al (1964), *PNAS* 51:1172, the contents of which are incorporated herein by reference. Such a procedure was performed with the recombinagenic TPB peptide toxin gene PCR products produced in Example 4. After incubation at 37° C., the reaction mixtures are added to cell cultures of host cells and plated on the appropriate media by mixing in 2 mls of molten top agar poured onto a hardened bottom agar. Plates are incubated at 37° for the *E coli* C600 gram-negative bacteria, and 30° C. for the *B. subtilis* 1L32 gram-positive bacteria. Plaques are screened for incorporation of the TPB peptide using Southern hybridization techniques. Plaques identified as positive are isolated and stocks are prepared from the single plaques. Chromosomal DNA isolated from these stocks is analyzed by restriction digestion, followed by sequencing.

EXAMPLE 6

In Vivo Homologous Recombination of an Intracellular Peptide Toxin Gene into a Bacteriophage Genome The homologous recombination event can be manipulated in vivo with competent bacterial cells lysogenic for the chosen bacteriophage. Competent *E coli* C600 gram-negative bacteria lysogenic for the wild-type lamba phage are prepared using the calcium chloride method, as described in *Molecular Cloning* (1989), 2$^{nd}$ Ed., Sambrook et al., Eds., Cold Spring Harbor Press, the contents of which are incorporated herein by reference. Competent *B. Subtilis* 1L32 lysogenic for phi-105 phage are prepared using methods described by Errington & Mandelstam (1983), *Journal of General Microbiology* 129:2091, the contents of which are incorporated herein by reference. The recombinagenic PCR product containing the intracellular peptide toxin gene is added to the competent bacterial cells and heat shocked as described in Sambrook et al., supra. After a one hour incubation at 37° C., the reaction mixtures are added to cell cultures of host cells and plated on the appropriate media by mixing in 2 mls of molten top agar poured onto a hardened bottom agar. Plates are incubated at 37° for the *E coli* C600 gram-negative bacteria, and 30° C. for the *B. subtilis* 1L32 gram-positive bacteria. Plaques are screened for incorporation of the TPB peptide using Southern hybridization techniques. Plaques identified as positive are isolated and stocks are prepared from the single plaques. Chromosomal DNA isolated from these stocks is analyzed by restriction digestion, followed by sequencing.

EXAMPLE 7

Use of a Toxin-Phage Bacteriocide to Kill Bacteria

To test the effectiveness of TPB peptide toxin A, lambda phage (American Type Culture Collection (ATCC) Accession No. 23724-B2) was engineered to express TPB peptide toxin A. This modified phage killed 100% of *E. coli* (ATCC Accession No. 23724). No lysogenic colonies were observed.

In addition, phi-105 phage (BGSC Accession No. 1A304 (phi105); Ohio State University, Columbus, Ohio) was engineered to express TPB peptide toxin A. This modified phage killed 100% of *B. subtilis* (BGSC Accession No. 1L32). No lysogenic clones were observed.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated nucleic acid molecule comprising a nucleotide sequence encoding a polypeptide comprising the amino acid sequence of SEQ ID NO: 2 and a bacterial promoter sequence.

2. The isolated nucleic acid molecule of claim 1 further comprising a nucleotide sequence encoding a bacteriophage coat protein.

3. The isolated nucleic acid molecule of claim 1 wherein the bacterial promoter sequence directs transcription in gram positive bacteria.

4. The isolated nucleic acid molecule of claim 1 wherein the bacterial promoter sequence directs transcription in gram negative bacteria.

5. A genetically engineered bacteriophage comprising a heterologous nucleic acid sequence encoding a polypeptide comprising the amino acid sequence of SEQ ID NO: 2.

6. A method for providing a genetically engineered bacteriophage comprising a heterologous nucleic acid molecule encoding a polypeptide comprising the amino acid sequence of SEQ ID NO: 2, the method comprising:

(a) providing an isolated nucleic acid molecule comprising a 5' region, a central region and a 3' region, the 5' region and the 3' region comprising nucleotide sequences present in a selected bacteriophage genome, the central region comprising a nucleotide sequence encoding a polypeptide comprising the amino acid sequence of SEQ ID NO: 2;

(b) contacting a bacterial cell lysogenic for the selected bacteriophage genome with the isolated nucleic acid molecule such that the isolated nucleic acid is introduced into the bacterial cell; and (c) allowing the isolated nucleic acid molecule to recombine with the bacteriophage genome present in the bacterial cell, thereby producing a genetically engineered bacteriophage comprising a heterologous nucleic acid molecule encoding a polypeptide comprising the amino acid sequence of SEQ ID NO: 2.

7. A method for providing a genetically engineered bacteriophage comprising a heterologous nucleic acid molecule encoding a polypeptide comprising the amino acid sequence of SEQ ID NO: 2, the method comprising:

(a) providing an isolated nucleic acid molecule comprising a 5' region, a central region and a 3' region, the 5' region and the 3' region comprising nucleotide sequences present in a selected bacteriophage genome, the central region comprising a nucleotide sequence encoding a polypeptide comprising the amino acid sequence of SEQ ID NO: 2;

(b) contacting a bacterial cell lysate with the isolated nucleic acid molecule and with an isolated DNA molecule comprising the selected bacteriophage genome; and (c) allowing the isolated nucleic acid molecule to recombine with the isolated DNA molecule comprising the bacteriophage genome and subsequently form bacteriophage particles, thereby producing a genetically engineered bacteriophage comprising a heterologous nucleic acid molecule encoding a polypeptide comprising the amino acid sequence of SEQ ID NO: 2.

8. A method for producing bacteriophage for reducing the viability of a selected type of bacteria, the method comprising:

(a) identifying a bacteriophage that is capable of infecting a selected type of bacteria;

(b) preparing a genetically engineered bacteriophage genome comprising a nucleic acid sequence that encodes a polypeptide comprising the amino acid sequence of SEQ ID NO: 2 and the genome of the identified bacteriophage; and (c) preparing bateriophage comprising the genetically engineered bacteriophage genome.

9. A composition comprising a genetically engineered bacteriophage comprising a heterologous nucleic acid molecule encoding a polypeptide comprising the amino acid sequence of SEQ ID NO: 2 and a pharmaceutically acceptable carrier.

* * * * *

UNITED STATES PATENT AND TRADEMARK OFFICE
CERTIFICATE OF CORRECTION

PATENT NO. : 6,759,229 B2
APPLICATION NO. : 10/025598
DATED : July 6, 2004
INVENTOR(S) : Diane L. Schaak It is certified that error appears in the above-identified patent and that said Letters Patent is hereby corrected as shown below:

At Col. 7, line 34, replace "infection" with --Infection--.

At Col. 8, line 1, replace "an" with --a--.

At Col. 8, lines 20-23, replace the sequence "GCGTCCGGCGTAGAGGATC-CAAGCTTTAATTTAAATTTTATTTGACAAAAATGGGCTCGTGTTGTACAAAT-GTATGGATTG-GCTGAAAGCTCGGGTTGAACAGG" with the following sequence, including underlining the relevant parts of the sequence as shown:
--<u>GCGTCCGGCGTAGAGGATCCAAGCTTT</u>AATTTAAATTTTATTT-GACAAAAATGGGCTCGTGTTGTACAAATGT<u>ATGGATTGGCTGAAAGCTCGG-GTTGAACAGG</u>--.

At Col. 9, lines 9-10, replace the sequence "CCATCGATGGCCGCTCGAGCTAT-TATTTCTGGATTTCAG" with the following sequence, including underlining the relevant parts of the sequence as shown:
--<u>CCATCGATGGCCGCTCGAG</u>CTATTATTTCTGGATTTCAG--.

At Col. 11, lines 35-38, replace the sequence "CGGGAAGCTTGGATCCGCATAG-CAAAACGGACATCACTCCGTTTCAATGGAGGTGATGTCCGTTTTCCGC-TCGAGCTAT-TATTTCTGGATTTCAGC" with the following sequence, including underlining the relevant parts of the sequence as shown:
--<u>CGGGAAGCTTGGATCCGCATAG</u>CAAAACGGACATCACTCCGTTTCAAT-GGA GGTGATGTCCGTTTT<u>CCGCTCGAGCTATTATTTCTGGATTTCAGC</u>--.

At Col. 12, lines 49-53, replace the sequence "CCG-GAATTCGCTAGCGGGCCCGAGTTGC-CCATATCGATGGGCAACTCATGCAAT TATTGT-GAGAAGCTTTAATTTAAATTTTATTTGACAAAAATGGG" with the following sequence, including underlining the relevant parts of the sequence as shown and including deleting the space near the middle of the sequence:
--<u>CCGGAATTCGCTAGCGGGCCCGAGTTGC</u>CCATATCGATGGGCAACT-CATGCAATTATTGTGAG<u>AAGCTTT</u>AATTTAAATTTTATTTGACAAAAAT-GGG--.

At Col. 13, line 54, replace "VegI/II" with --VegI/II--.

UNITED STATES PATENT AND TRADEMARK OFFICE
CERTIFICATE OF CORRECTION

PATENT NO. : 6,759,229 B2
APPLICATION NO. : 10/025598
DATED : July 6, 2004
INVENTOR(S) : Diane L. Schaak It is certified that error appears in the above-identified patent and that said Letters Patent is hereby corrected as shown below:

At Col. 13, lines 59-62, replace the sequence "CGC-CCTAGGCGGCCGAGGACCCTACTTTAG-GCATTTATACTCCGCTGGAAGCGC GTGTGTATTG-GCATGCATCGATTAGTAAAACGGACATCACTCCG" with the following sequence, including underlining the relevant parts of the sequence as shown and including deleting the space near the middle of the sequence:
--<u>CGCCCTAGGCGGCCGAGGACCC</u>TACTTTAGGCATTTATACTCCGCTGGAAGCGCGTGTGTATT<u>GGCATGCATCGATTAGT</u>AAAACGGACATCACTCCG--.

At Col. 15, lines 51-54, replace the sequence "CCG-GAATTCGCTAGCGGGCCCGAGGGGTAGT-TGCATACCACTAAAGATGTTCAG GTGCACAT-GAAGCTTTAATTTAAATTTTATTTGACAAAAATGGG" with the following sequence, including underlining the relevant parts of the sequence as shown and including deleting the space near the middle of the sequence:
--<u>CCGGAATTCGCTAGCGGGCCCGAGGGGT</u>AGTTGCATACCACTAAAGATGTTCAGGTGCACATG<u>AAGCTTT</u>AATTTAAATTTTATTTGACAAAAATGGG--.

At Col. 15, line 60, replace "to-determine" with --to determine--.

At Col. 16, line 62, replace "Phi-1 05" with --Phi-105--.

At Col. 16, lines 63-65, replace the sequence "CGCCCTAGGCGGCCGAGGACCCGGTTTC-CCTTCCCCCTAAAGCGTTCCTTTCCTC CAATGCTG-GCATGCATCGATTAGTAAAACGGACATCACTCCG" with the following sequence, including underlining the relevant parts of the sequence as shown and including deleting the space near the middle of the sequence:
--<u>CGCCCTAGGCGGCCGAGGACCC</u>GGTTTCCCTTCCCCCTAAAGCGTTCCTTTCCTCCAATGCT<u>GGCATGCATCGATTAGT</u>AAAACGGACATCACTCCG--.

UNITED STATES PATENT AND TRADEMARK OFFICE
CERTIFICATE OF CORRECTION

PATENT NO. : 6,759,229 B2 Page 3 of 3
APPLICATION NO. : 10/025598
DATED : July 6, 2004
INVENTOR(S) : Diane L. Schaak It is certified that error appears in the above-identified patent and that said Letters Patent is hereby corrected as shown below:

At Col. 18, line 44, replace "a" with --an--.

Signed and Sealed this

Twenty-fifth Day of September, 2007

JON W. DUDAS
*Director of the United States Patent and Trademark Office*

SEQUENCE LISTING

```
<160> NUMBER OF SEQ ID NOS: 16

<210> SEQ ID NO 1
<211> LENGTH: 117
<212> TYPE: DNA
<213> ORGANISM: Artificial Sequence
<220> FEATURE:
<223> OTHER INFORMATION: Synthetically generated primer
<220> FEATURE:
<221> NAME/KEY: CDS
<222> LOCATION: (1)...(117)

<400> SEQUENCE: 1 atg gat tgg ctg aaa gct cgg gtt gaa cag gaa ctg cag gct ctg gaa      48
Met Asp Trp Leu Lys Ala Arg Val Glu Gln Glu Leu Gln Ala Leu Glu
 1               5                  10                  15 gca cgt ggt acc gat tcc aac gct gag ctg cgg gct atg gaa gct aaa      96
Ala Arg Gly Thr Asp Ser Asn Ala Glu Leu Arg Ala Met Glu Ala Lys
             20                  25                  30 ctt aag gct gaa atc cag aag                                         117
Leu Lys Ala Glu Ile Gln Lys
         35

<210> SEQ ID NO 2
<211> LENGTH: 39
<212> TYPE: PRT
<213> ORGANISM: Artificial Sequence
<220> FEATURE:
<223> OTHER INFORMATION: Synthetically generated peptide

<400> SEQUENCE: 2

Met Asp Trp Leu Lys Ala Arg Val Glu Gln Glu Leu Gln Ala Leu Glu
 1               5                  10                  15

Ala Arg Gly Thr Asp Ser Asn Ala Glu Leu Arg Ala Met Glu Ala Lys
             20                  25                  30

Leu Lys Ala Glu Ile Gln Lys
         35

<210> SEQ ID NO 3
```

```
<211> LENGTH: 104
<212> TYPE: DNA
<213> ORGANISM: Artificial Sequence
<220> FEATURE:
<223> OTHER INFORMATION: Synthetically generated primer

<400> SEQUENCE: 3
gcgtccggcg tagaggatcc aagctttaat ttaaatttta tttgacaaaa atgggctcgt    60
gttgtacaaa tgtatggatt ggctgaaagc tcgggttgaa cagg                    104

<210> SEQ ID NO 4
<211> LENGTH: 39
<212> TYPE: DNA
<213> ORGANISM: Artificial Sequence
<220> FEATURE:
<223> OTHER INFORMATION: Synthetically generated primer

<400> SEQUENCE: 4
ccatcgatgg ccgctcgagc tattatttct ggatttcag                          39

<210> SEQ ID NO 5
<211> LENGTH: 17
<212> TYPE: DNA
<213> ORGANISM: Artificial Sequence
<220> FEATURE:
<223> OTHER INFORMATION: Synthetically generated primer

<400> SEQUENCE: 5
ggcgtatcac gaggccc                                                  17

<210> SEQ ID NO 6
<211> LENGTH: 19
<212> TYPE: DNA
<213> ORGANISM: Artificial Sequence
<220> FEATURE:
<223> OTHER INFORMATION: Synthetically generated primer

<400> SEQUENCE: 6
gtggcgccgg tgatgccgg                                                19

<210> SEQ ID NO 7
<211> LENGTH: 39
<212> TYPE: DNA
<213> ORGANISM: Bacteriophage lambda

<400> SEQUENCE: 7
ttgcccatat cgatgggcaa ctcatgcaat tattgtgag                          39

<210> SEQ ID NO 8
<211> LENGTH: 42
<212> TYPE: DNA
<213> ORGANISM: Bacteriophage lambda

<400> SEQUENCE: 8
caatacacac gcgcttccag cggagtataa atgcctaaag ta                      42

<210> SEQ ID NO 9
<211> LENGTH: 39
<212> TYPE: DNA
<213> ORGANISM: Bacteriophage phi-165

<400> SEQUENCE: 9
gggtagttgc ataccactaa agatgttcag gtgcacatg                          39
```

<210> SEQ ID NO 10
<211> LENGTH: 40
<212> TYPE: DNA
<213> ORGANISM: Bacteriophage phi-165

<400> SEQUENCE: 10
agcattggag gaaaggaacg ctttaggggg aagggaaacc                               40

<210> SEQ ID NO 11
<211> LENGTH: 38
<212> TYPE: DNA
<213> ORGANISM: Artificial Sequence
<220> FEATURE:
<223> OTHER INFORMATION: Synthetically generated primer

<400> SEQUENCE: 11
cgtccggcgt agaggatcca agctttaatt taaatttt                                38

<210> SEQ ID NO 12
<211> LENGTH: 96
<212> TYPE: DNA
<213> ORGANISM: Artificial Sequence
<220> FEATURE:
<223> OTHER INFORMATION: Synthetically generated primer

<400> SEQUENCE: 12
cgggaagctt ggatccgcat agcaaaacgg acatcactcc gtttcaatgg aggtgatgtc        60
cgttttccgc tcgagctatt atttctggat ttcagc                                  96

<210> SEQ ID NO 13
<211> LENGTH: 98
<212> TYPE: DNA
<213> ORGANISM: Artificial Sequence
<220> FEATURE:
<223> OTHER INFORMATION: Synthetically generated primer

<400> SEQUENCE: 13
ccggaattcg ctagcgggcc cgagttgccc atatcgatgg gcaactcatg caattattgt        60
gagaagcttt aatttaaatt ttatttgaca aaaatggg                                98

<210> SEQ ID NO 14
<211> LENGTH: 98
<212> TYPE: DNA
<213> ORGANISM: Artificial Sequence
<220> FEATURE:
<223> OTHER INFORMATION: Synthetically generated primer

<400> SEQUENCE: 14
cgccctaggc ggccgaggac cctactttag gcatttatac tccgctggaa gcgcgtgtgt        60
attggcatgc atcgattagt aaaacggaca tcactccg                                98

<210> SEQ ID NO 15
<211> LENGTH: 98
<212> TYPE: DNA
<213> ORGANISM: Artificial Sequence
<220> FEATURE:
<223> OTHER INFORMATION: Synthetically generated primer

<400> SEQUENCE: 15
ccggaattcg ctagcgggcc cgaggggtag ttgcatacca ctaaagatgt tcaggtgcac        60
atgaagcttt aatttaaatt ttatttgaca aaaatggg                                98

<210> SEQ ID NO 16

```
<211> LENGTH: 97
<212> TYPE: DNA
<213> ORGANISM: Artificial Sequence
<220> FEATURE:
<223> OTHER INFORMATION: Synthetically generated primer

<400> SEQUENCE: 16
cgccctaggc ggccgaggac ccggtttccc ttccccctaa agcgttcctt tcctccaatg      60
ctggcatgca tcgattagta aaacggacat cactccg                              97
```